US00PP14109P39

(12) United States Plant Patent
Gilford et al.

(10) Patent No.: US PP14,109 P3
(45) Date of Patent: Aug. 26, 2003

(54) STRAWBERRY PLANT NAMED MADEIRA

(75) Inventors: Kristie L. Gilford, Dover, FL (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/968,558

(22) Filed: Oct. 1, 2001

(65) Prior Publication Data

US 2003/0079264 P1 Apr. 24, 2003

(51) Int. Cl.[7] ..... A01H 5/00

(52) U.S. Cl. ..... Plt./209

(58) Field of Search ..... Plt./209, 208

*Primary Examiner*—Bruce R. Campell
*Assistant Examiner*—Anne Marie Grünberg
(74) *Attorney, Agent, or Firm*—Pennie & Edmonds, LLP

(57) ABSTRACT

This invention relates to a new and distinct variety of strawberry named 'Madeira'. The variety is distinguished by its flat habit, dense plant density, obtuse terminal leaflet shape, reflexed pose of calyx segments, downward pose of petiole hairs, same size calyx in relation to fruit on the secondary fruit, and fruit with weak to medium acidity.

5 Drawing Sheets

Latin name: The Latin name of the plant is *Fragaria× ananassa.*

Variety denomination: The varietal denomination of the plant is 'Maderia'.

BACKGROUND OF THE INVENTION

The new variety originated as a result of a controlled cross between the strawberry 7C171 and 21Y13 (both unpatented varieties) in an ongoing breeding program, and was discovered as a seedling in a controlled breeding plot in Hillsborough County, Florida in December, 1997. The original seedling was asexually propagated by stolons in a nursery in Shasta County, Calif. Propagules were transplanted to a controlled breeding plot in Hillsborough County, Fla. where the variety was identified and selected for further evaluation. Madeira was subsequently asexually propagated and underwent further testing in Hillsborough County, Fla. for five years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Madeira'. The variety is botanically identified as *Fragaria×ananassa*. The new variety is distinguished from other varieties by a number of characteristics as set forth in Tables 1–4.

COMPARISON TO SIMILAR VARIETIES

The varieties which we believe to be similar to Madeira from those known to us are 'Biscayne' (U.S. patent application Ser. No. 09/396,214 filed Sep. 15, 1999) and 'Marathon' (U.S. patent application Ser. No. 09/396,213 filed Sep. 15, 1999). There are several characteristics of the new variety that are different from, or not possessed by Biscayne or Marathon. The base of the terminal leaflet shape is obtuse.

The pose of the petiole hairs is downwards. The size of the calyx in relation to fruit on the secondary fruit is smaller.

In addition, there are several characteristics of the new variety that are different from, or not possessed by 21Y13 and 7C171, the antecedents of Madeira. Madiera differs from 21Y13 in that it is partially everbearing, while 21Y13 was a day-neutral variety. Madeira differs from 7C171 by having superior shipability.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
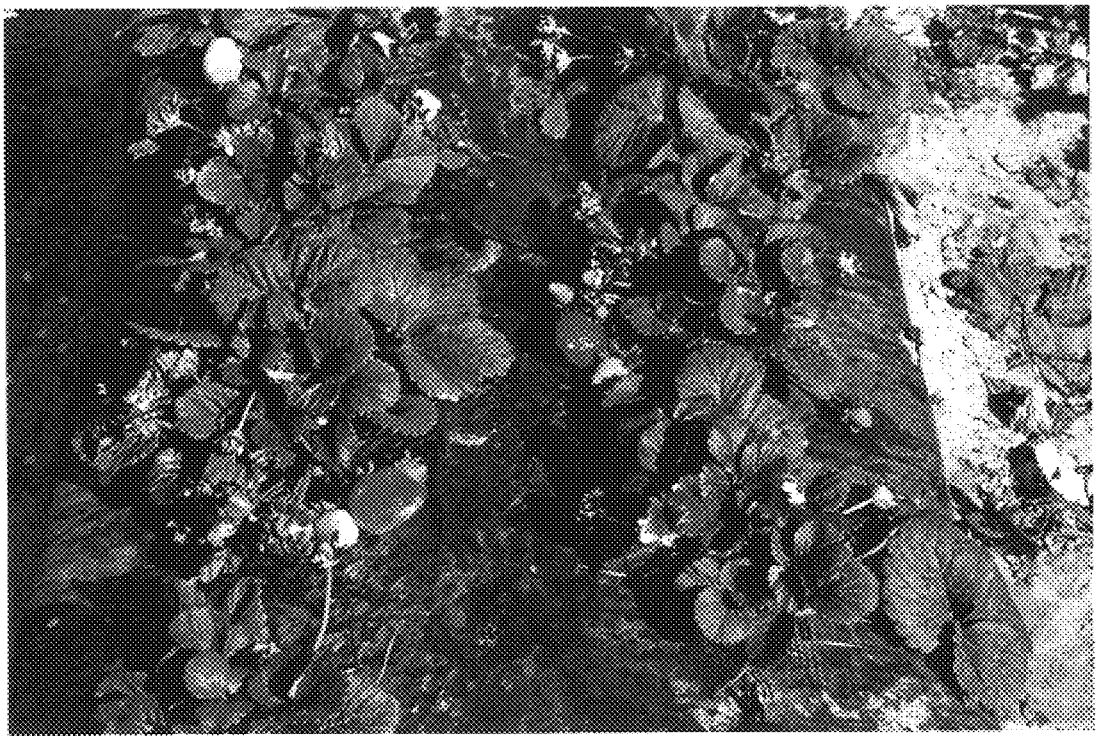
FIG. 1 shows the whole plant.
Figure 2:
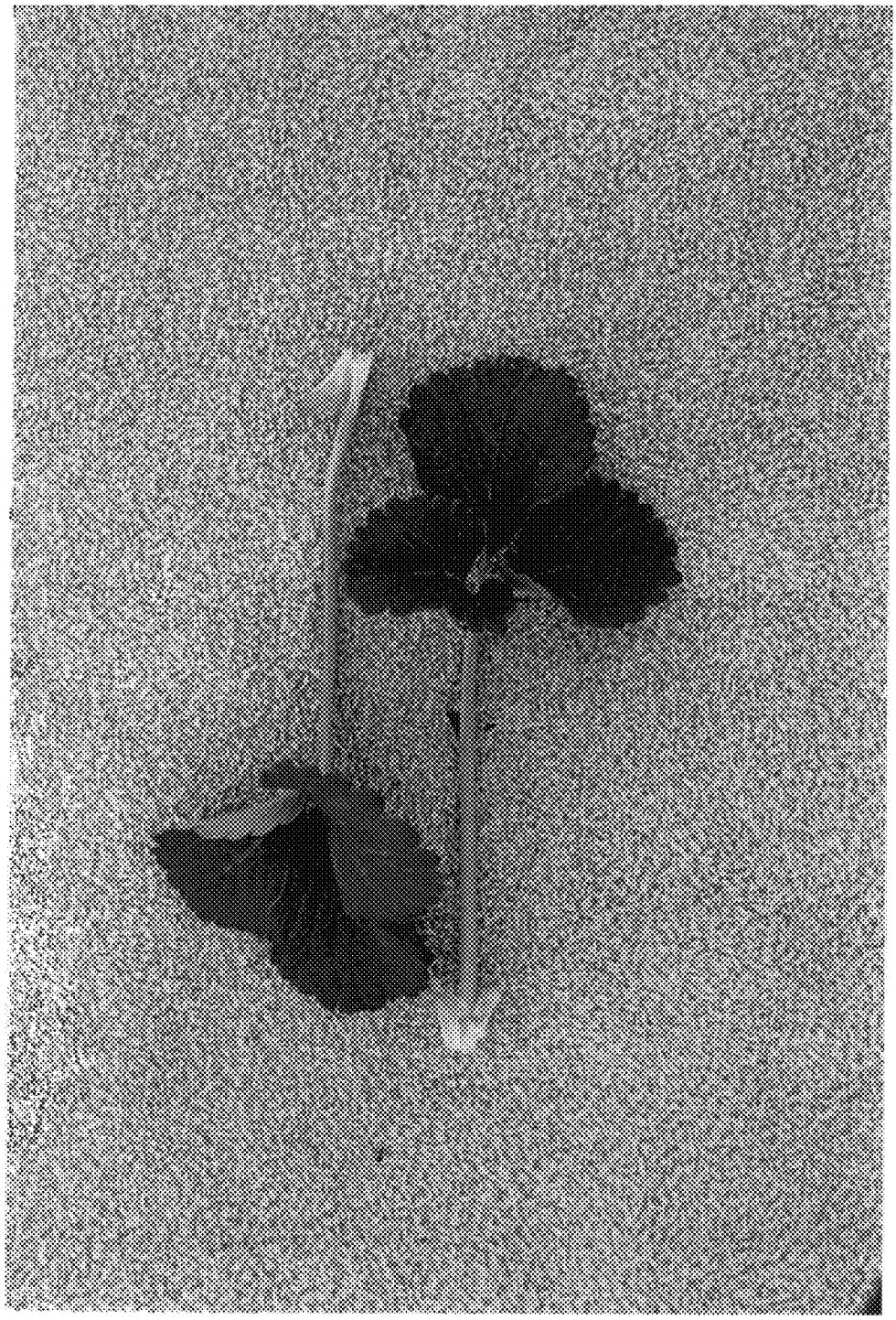
FIG. 2 shows the leaves of the plant.
Figure 3:
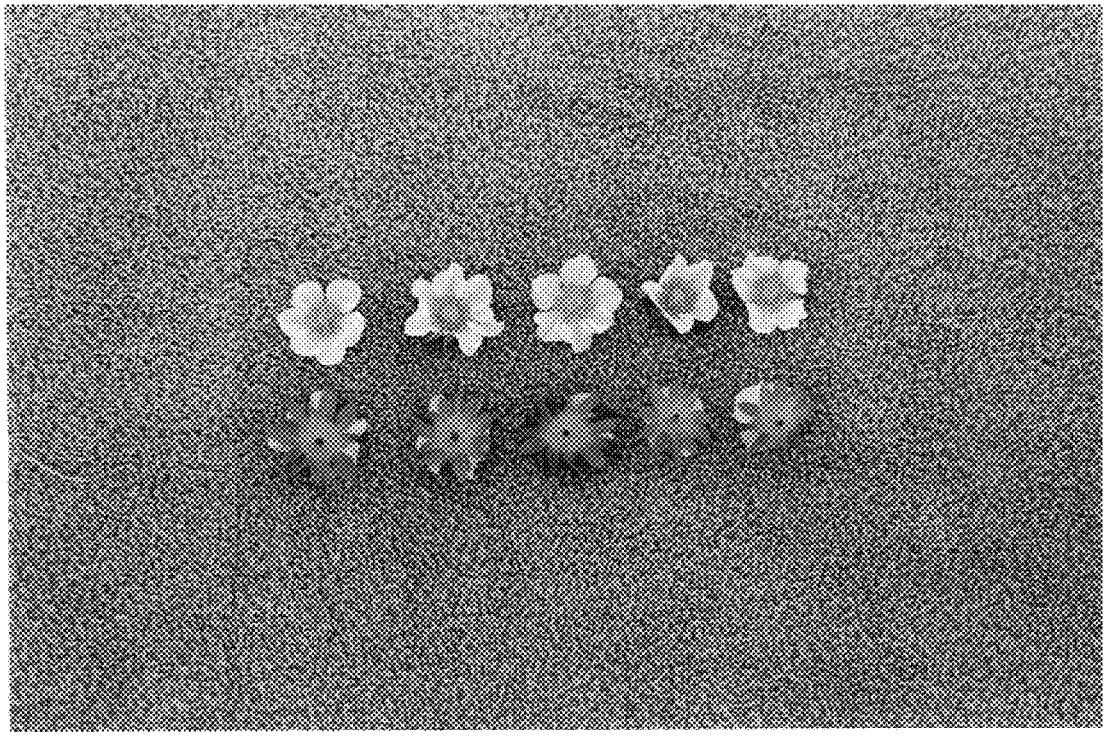
FIG. 3 shows the upper side and the under side of the flowers.
Figure 4:
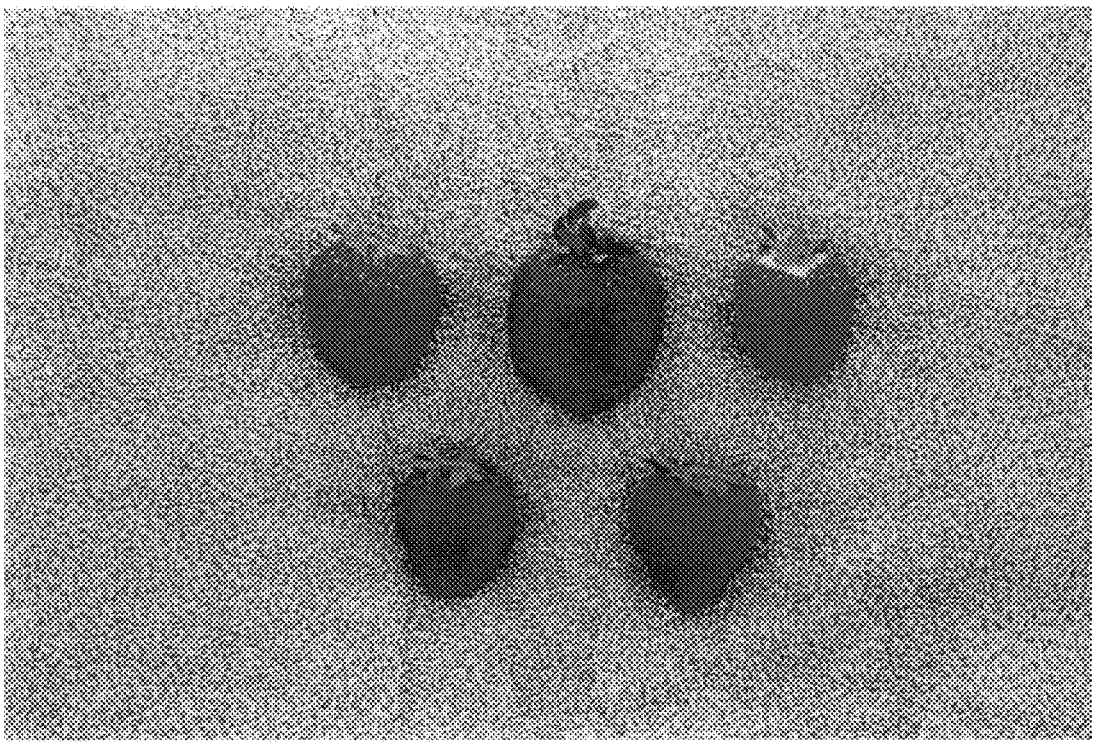
FIG. 4 shows a close-up of the fruit.
Figure 5:
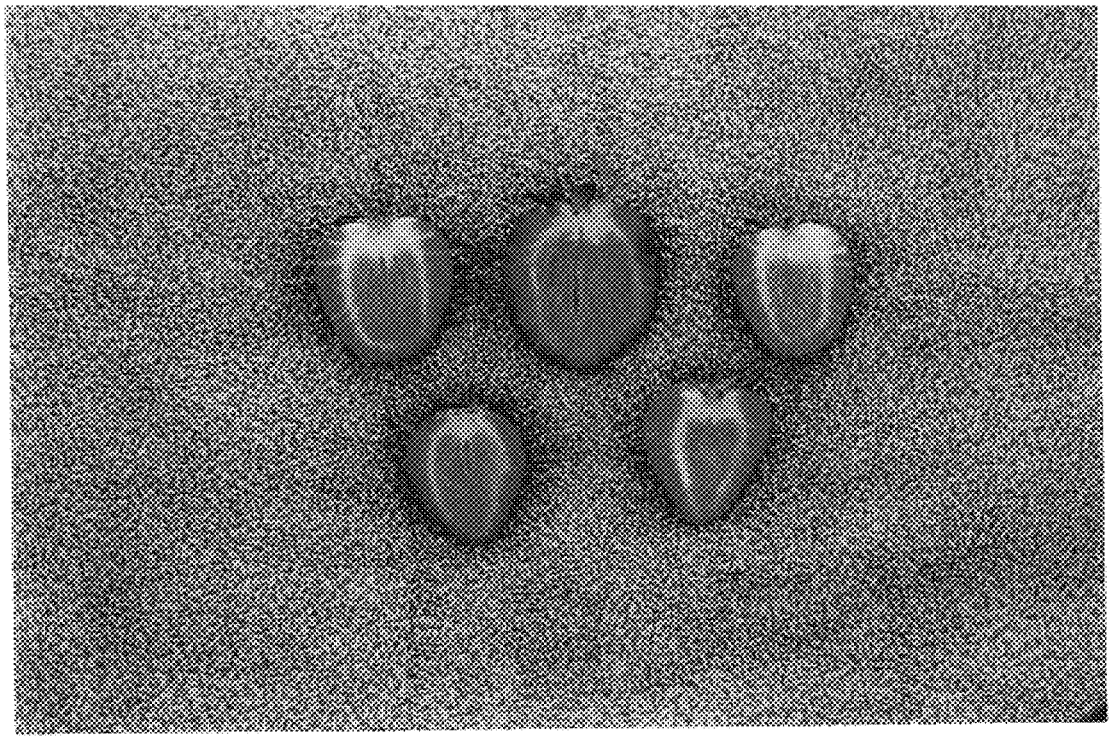
FIG. 5 shows the fruit in longitudinal cross-section.

The following detailed description of the new variety is based upon observations taken of plants and fruit grown in Hillsborough, Fla. USA. Observations of Madeira, Marathon, and Biscayne were taken in side by side comparison in January, 2001. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons or by tissue culture. Although propagation by stolons or tissue culture is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The petal color of Madeira is white, 155C in The R.H.S. Color Chart. The fruit described is the secondary fruit on one year old plants. Fruit and flower measurements are an average of both primary and secondary fruit and flowers.

Table 1 provides information on the plant and fruit characteristics of the new variety Madeira compared with characteristics of Marathon and Biscayne. Table 2 provides additional information of the plant and fruit characteristics of the new variety Madeira compared with characteristics of the varieties Marathon and Biscayne. Table 3 provides information of the new variety's reaction to pests and diseases, respectively, compared to the varieties Marathon and Biscayne. Table 4 provides isozyme characteristics of the new variety as compared to the varieties Marathon and Biscayne.

TABLE 1

DETAILED COMPARISON OF MADEIRA, BISCAYNE AND MARATHON

| | Madeira | Biscayne | Marathon |
|---|---|---|---|
| Plant Characteristics | | | |
| Height of Plant (cm) | 17 | 13.7 | 14.3 |
| Spread of Plant (cm) | 28.2 | 32.7 | 34.1 |
| Number of Crowns | 4.8 | 6.9 | 6.0 |
| Leaf Characteristics | | | |
| Terminal Leaflet Length (cm) | 8.0 | 6.9 | 8.8 |
| Terminal Leaflet Width (cm) | 7.0 | 7.2 | 8.3 |
| Terminal Leaflet Length/Width Ratio | 1.14 | 0.96 | 1.06 |
| # Teeth/Terminal Leaflet | 19.9 | 26.0 | 25.7 |
| Color of upper side | 147A dark green | 137A light green | 137B light green |
| Color of under side | 137B light gray green | 139C light gray green | 139C light gray green |
| Petiole Length (cm) | 11.6 | 11.4 | 11.9 |
| Petiole Color | 145A yellow-green | 141D yellow-green | 144B yellow-green |
| Bract Frequency | 90% mostly paired | 100% | 80% mostly paired |
| Stipule Length (cm) | 3.6 | 3.6 | 3.3 |
| Stipule Width (cm) | 2.6 | 2.0 | 2.1 |
| Flower Characteristics | | | |
| Petal Length (cm) | 1.55 | 1.29 | 1.47 |
| Petal Width (cm) | 1.36 | 1.45 | 1.66 |
| Petal Length/Width Ratio | 1.14 | 0.89 | 0.89 |
| Flower Diameter (cm) | 3.6 | 3.36 | 4.14 |
| Calyx Diameter (cm) | 3.08 | 4.17 | 4.82 |
| Flower Color | 155C white | 155C white | 155C white |
| Fruit Characteristics | | | |
| Fruit Length (cm) | 4.9 | 4.1 | 4.6 |
| Fruit Width (cm) | 4.3 | 3.9 | 4.0 |

TABLE 1-continued

DETAILED COMPARISON OF MADEIRA, BISCAYNE AND MARATHON

| | Madeira | Biscayne | Marathon |
|---|---|---|---|
| Fruit Length/Width Ratio | 1.15 | 1.06 | 1.13 |
| Average Berry Weight (g) | 19 | 18 | 26 |
| External Color | 46A dark red | 46B red | 42A orange red |
| Internal Color | 43A medium red | 44A medium red | 42C light red |
| Achene Coloration | 12A to 178B yellow to dark red | 13B to 46A yellow to red | 12A to 46A yellow to red |
| Yield (g/plant) | 432 | 335 | 539 |

TABLE 2

CHARACTERISTICS OF MADEIRA, BISCAYNE AND MARATHON

| | Madeira | Biscayne | Marathon |
|---|---|---|---|
| Plant | | | |
| Habit | flat globose | flat globose | flat globose |
| Density | medium | medium | medium |
| Vigor | strong | strong | strong |
| Leaf | | | |
| Shape in cross section | concave | concave | concave |
| Interveinal blistering | medium | weak | medium |
| Glossiness | medium | medium | medium |
| Number of leaflets | three only | three only | three only |
| Terminal leaflet margin profile | revolute | revolute | revolute |
| Terminal leaflet shape of base | obtuse | rounded | slightly oblique |
| Terminal leaflet shape of teeth | rounded | rounded | obtuse |
| Stipule pubescence | medium | medium | medium |
| Petiole pubescence | medium | medium | medium |
| Petiole pose of hairs | downwards | outwards | outwards |
| Stolon | | | |
| Number | many | many | medium to many |
| Anthocyanin coloration | strong to very strong | strong | medium to strong |
| Thickness | medium to thick | medium | medium to thick |
| Pubescence | medium | medium | sparse |
| Inflorescence | | | |
| Position relative to foliage | beneath | level | beneath |
| Diameter of calyx relative to corolla on secondary flowers | larger | larger | larger |
| Diameter of inner calyx relative to outer on secondary flowers | same size | same size | same size |
| Spacing of petals | overlapping | overlapping | overlapping |
| Fruiting Truss | | | |
| Fruiting Truss Length (cm) | 13.7 | 17.1 | 18.3 |
| Attitude at first picking | prostrate | prostrate | prostrate |
| Fruit | | | |
| Predominant shape | conical | conical | cordate |

TABLE 2-continued

CHARACTERISTICS OF MADEIRA, BISCAYNE AND MARATHON

| | Madeira | Biscayne | Marathon |
|---|---|---|---|
| Difference in shapes between primary and secondary fruits | slight | slight | slight |
| Band without achenes | narrow | narrow | narrow |
| Unevenness of surface | weak | weak | weak |
| Evenness of color | even | even | slightly uneven |
| Glossiness | strong | strong | strong |
| Insertion of achenes | level with surface | level with surface | below surface |
| Insertion of calyx | level | level | level |
| Pose of the calyx segments | reflexed | spreading | spreading |
| Size of calyx in relation to fruit on secondary fruit | smaller | larger | larger |
| Adherence of calyx | strong | strong | strong |
| Finnness of flesh | medium | firm | medium |
| Evenness of flesh color | slightly uneven | slightly uneven | slightly uneven |
| Distribution of flesh color | marginal and central | marginal and central | marginal and central |
| Hollow center size | medium | large | medium |
| Sweetness | weak to medium | strong | weak to medium |
| Texture when tasted | fine | fine | fine |
| Acidity | weak to medium | medium | medium |
| Time of Flowering | very early | early | very early |
| Harvest Interval | Late-November through Mid-April | Early-December through Mid-April | Early-December through Mid-April |
| Type of Bearing | partially everbearing | partially everbearing | partially everbearing |

PEST AND DISEASE RESISTANCE AND SUSCEPTIBILITY

TABLE 3

| | Madeira | Biscayne | Marathon |
|---|---|---|---|
| Reaction to Pests | | | |
| *Tetranychus urticae* | susceptible | susceptible | susceptible |
| Aphis spp. | susceptible | susceptible | susceptible |
| *Lygus hesperus* | susceptible | susceptible | susceptible |
| Reaction To Diseases | | | |
| Botrytis fruit rot | moderately susceptible | moderately susceptible | moderately susceptible |
| Powdery mildew | moderately susceptible | susceptible | susceptible |
| Verticillium wilt | moderately resistant | susceptible | susceptible |
| Strawberry Mottle Virus | moderately resistant | moderately resistant | moderately resistant |
| *Xanthomonas fragariae* | moderately susceptible | moderately susceptible | moderately susceptible |

ISOZYME ANALYSIS

In addition to the morphological description above, the new cultivar, Madeira, has been analyzed to obtain an indication of its genetic makeup to provide further means for identifying the new variety and distinguishing it from some other somewhat similar and/or related strawberry varieties. Specifically, leaf samples of Madeira, Biscayne, and Marathon were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR MADEIRA, BISCAYNE AND MARATHON

| Locus | Madeira | Biscayne | Marathon |
|---|---|---|---|
| PGI | A1 | A1 | A1 |
| LAP | B1 | B3 | B3 |
| PGM | C2 | C4 | C4 |

What is claimed is:

1. A new and distinct variety of strawberry plant, substantially as shown and described.

* * * * *